United States Patent
Gong et al.

(10) Patent No.: US 8,940,356 B2
(45) Date of Patent: Jan. 27, 2015

(54) MAINTAINING A FIXED DISTANCE DURING COATING OF DRUG COATED BALLOON

(75) Inventors: Victoria M. Gong, Sunnyvale, CA (US); Stephen D. Pacetti, San Jose, CA (US); Anthony S. Andreacchi, San Jose, CA (US); Michael Leonard, Palo Alto, CA (US); Binh T. Nguyen, Newark, CA (US); John Stankus, Campbell, CA (US); Dan Cox, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 299 days.

(21) Appl. No.: 13/109,156

(22) Filed: May 17, 2011

(65) Prior Publication Data

US 2011/0281020 A1   Nov. 17, 2011

Related U.S. Application Data

(60) Provisional application No. 61/345,569, filed on May 17, 2010.

(51) Int. Cl.
*A61L 33/00* (2006.01)
*A61M 25/10* (2013.01)
*B05C 5/02* (2006.01)
*B05D 1/26* (2006.01)
*A61F 2/958* (2013.01)
*B05B 13/02* (2006.01)
*B05D 1/00* (2006.01)
*B05D 3/02* (2006.01)

(52) U.S. Cl.
CPC ............ *A61M 25/1029* (2013.01); *B05C 5/022* (2013.01); *B05D 1/26* (2013.01); *A61F 2/958* (2013.01); *A61M 2025/1031* (2013.01); *B05B 13/0235* (2013.01); *B05D 1/002* (2013.01); *B05D 3/0254* (2013.01)
USPC .......... 427/2.1; 427/2.24; 427/2.28; 427/336; 427/426; 427/430.1; 427/2.3; 118/320; 118/620

(58) Field of Classification Search
USPC ............. 427/2.24, 2.28, 336, 426, 430.1, 2.3; 118/620, 320
See application file for complete search history.

(56) References Cited

U.S. PATENT DOCUMENTS 4,743,465 A   5/1988   Saeki et al.
4,748,982 A   6/1988   Horzewski et al.
(Continued)

OTHER PUBLICATIONS

PlumbingSupply.Com, Pipe Hangers and Brackets, Feb. 2001, www.plumbingsupply.com/pipehangers.html.*
(Continued)

*Primary Examiner* — Dah-Wei D Yuan
*Assistant Examiner* — Andrew Bowman
(74) *Attorney, Agent, or Firm* — Baker Botts LLP

(57) ABSTRACT

A system and method for coating an expandable member of a medical device comprising a support structure to support the expandable member and a dispenser positioned with at least one outlet proximate a surface of an expandable member. A drive assembly establishes relative movement between the at least one outlet and the surface of the expandable member to apply fluid on the surface of the expandable member along a coating path. A guide maintains a substantially fixed distance between the at least one outlet and the surface of the expandable member during relative movement therebetween by displacing the expandable member relative to the at least one outlet.

11 Claims, 9 Drawing Sheets

(56) References Cited

U.S. PATENT DOCUMENTS

| | | | |
|---|---|---|---|
| 5,300,085 | A | 4/1994 | Yock |
| 5,370,614 | A | 12/1994 | Amundson et al. |
| 5,464,650 | A | 11/1995 | Berg et al. |
| 5,496,346 | A | 3/1996 | Horzewski et al. |
| 5,591,227 | A | 1/1997 | Dinh et al. |
| 5,626,600 | A | 5/1997 | Horzewski et al. |
| 5,649,977 | A | 7/1997 | Campbell |
| 5,911,452 | A | 6/1999 | Yan |
| 5,980,972 | A * | 11/1999 | Ding ........................... 427/2.24 |
| 6,120,847 | A | 9/2000 | Yang et al. |
| 6,406,457 | B1 | 6/2002 | Wang et al. |
| 6,478,807 | B1 | 11/2002 | Foreman et al. |
| 6,494,906 | B1 | 12/2002 | Owens |
| 6,669,980 | B2 | 12/2003 | Hansen |
| 6,676,987 | B2 | 1/2004 | Zhong et al. |
| 6,743,462 | B1 | 6/2004 | Pacetti |
| 7,241,344 | B2 | 7/2007 | Worsham et al. |
| 7,335,227 | B2 | 2/2008 | Jalisi |
| 7,378,105 | B2 | 5/2008 | Burke et al. |
| 7,445,792 | B2 | 11/2008 | Toner et al. |
| 7,455,876 | B2 | 11/2008 | Castro et al. |
| 7,504,125 | B1 | 3/2009 | Pacetti et al. |
| 7,524,527 | B2 | 4/2009 | Stenzel |
| 2001/0021419 | A1 | 9/2001 | Luthje et al. |
| 2004/0062875 | A1 | 4/2004 | Chappa et al. |
| 2004/0073284 | A1 | 4/2004 | Bates et al. |
| 2004/0234748 | A1 | 11/2004 | Stenzel |
| 2005/0158449 | A1 | 7/2005 | Chappa |
| 2005/0196518 | A1 | 9/2005 | Stenzel |
| 2007/0031611 | A1 | 2/2007 | Babaev |
| 2007/0088255 | A1 | 4/2007 | Toner et al. |
| 2007/0179591 | A1 | 8/2007 | Baker et al. |
| 2008/0113081 | A1 | 5/2008 | Hossainy et al. |
| 2009/0226598 | A1 | 9/2009 | Feng et al. |
| 2010/0023108 | A1 | 1/2010 | Toner et al. |
| 2010/0030183 | A1 | 2/2010 | Toner et al. |
| 2010/0040766 | A1 * | 2/2010 | Chappa et al. ................. 427/2.3 |
| 2010/0055294 | A1 | 3/2010 | Wang et al. |
| 2011/0151199 | A1 | 6/2011 | Nelson et al. |
| 2011/0281019 | A1 | 11/2011 | Gong et al. |
| 2012/0022540 | A1 | 1/2012 | Chasmawala et al. |
| 2012/0064223 | A1 | 3/2012 | Gamez et al. |
| 2012/0065583 | A1 | 3/2012 | Serna et al. |
| 2012/0128863 | A1 | 5/2012 | Nguyen et al. |
| 2012/0143054 | A1 | 6/2012 | Eaton et al. |
| 2012/0315374 | A1 | 12/2012 | Nguyen et al. |
| 2012/0315375 | A1 | 12/2012 | Shen et al. |
| 2012/0315376 | A1 | 12/2012 | Nguyen et al. |
| 2014/0113059 | A1 | 4/2014 | Shen et al. |

OTHER PUBLICATIONS

Unverdorben, Martin, "The Paclitaxel-Eluting PTCA-Balloon Catheter in Corornary Artery Disease PEPCAD I-SVD PEPCAD II-ISR", Clinical Research Institute, Center for Cardiovascular Diseases, 2005-2006, Rotenburg/Fulda, Germany.
U.S. Appl. No. 13/280,067, Apr. 26, 2013 Applicant Summary of Interview with Examiner.
U.S. Appl. No. 13/158,101, Apr. 26, 2013 Restriction Requirement.
U.S. Appl. No. 13/158,057, Apr. 26, 2013 Restriction Requirement.
U.S. Appl. No. 12/882,953, Apr. 12, 2013 Response to Non-Final Office Action.
U.S. Appl. No. 12/882,953, Jan. 15, 2013 Non-Final Office Action.
U.S. Appl. No. 12/882,953, Dec. 21, 2012 Response to Restriction Requirement.
U.S. Appl. No. 12/882,953, Nov. 28, 2012 Restriction Requirement.
U.S. Appl. No. 12/882,990, Apr. 8, 2013 Response to Non-Final Office Action.
U.S. Appl. No. 12/882,990, Dec. 6, 2012 Non-Final Office Action.
U.S. Appl. No. 13/108,283, Mar. 28, 2013 Non-Final Office Action.
U.S. Appl. No. 13/158,101, Oct. 7, 2013 Notice of Allowance.
U.S. Appl. No. 13/158,101, Sep. 17, 2013 Supplemental Amendment and Statement of the Substance of the Interview.
U.S. Appl. No. 13/108,283, Nov. 12, 2013 Issue Fee payment.
U.S. Appl. No. 13/108,283, Aug. 12, 2013 Notice of Allowance.
U.S. Appl. No. 12/882,990, Oct. 11, 2013 Advisory Action.
U.S. Appl. No. 12/882,990, Oct. 1, 2013 Response to Final Office Action.
U.S. Appl. No. 12/882,990, Aug. 1, 2013 Final Office Action.
U.S. Appl. No. 13/158,057, Oct. 24, 2013 Applicant Initiated Interview Summary.
U.S. Appl. No. 13/158,057, Sep. 12, 2013 Non-Final Office Action.
U.S. Appl. No. 12/882,953, Dec. 9, 2013 Notice of Allowance.
U.S. Appl. No. 12/882,953, Nov. 15, 2013 Request for Continued Examination (RCE).
U.S. Appl. No. 12/882,953, Oct. 28, 2013 Advisory Action.
U.S. Appl. No. 12/882,953, Oct. 16, 2013 Response to Final Office Action.
U.S. Appl. No. 12/882,953, Aug. 16, 2013 Final Office Action.
Vivekanandhan, et al., "Computer-Aided Torch Trajectory Generation for Automated Coating of Parts with Complex Surfaces", *Journal of Thermal Spray Technology*, 3(2):208-215 (1994).
Cornell, Maintaining Distance Using Sonar video, Youtube (2010) http://www.youtube.com/watch?v=Pj6Jxo2Sqgw, [Downloaded on Sep. 16, 2013].
U.S. Appl. No. 14/078,212, filed Nov. 12, 2013.
U.S. Appl. No. 12/882,953, Mar. 7, 2014 Issue Fee payment.
U.S. Appl. No. 12/882,990, Dec. 19, 2013 Non-Final Office Action.
U.S. Appl. No. 13/158,131, Mar. 13, 2014 Non-Final Office Action.
U.S. Appl. No. 14/078,212, Jun. 6, 2014 Non-Final Office Action.

* cited by examiner

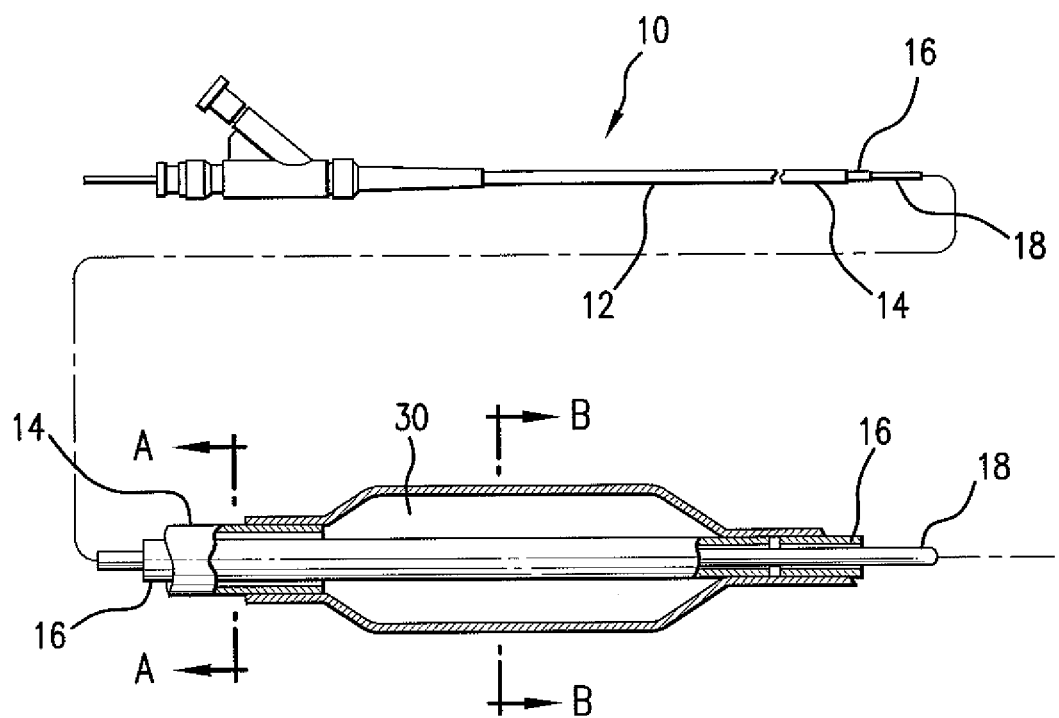
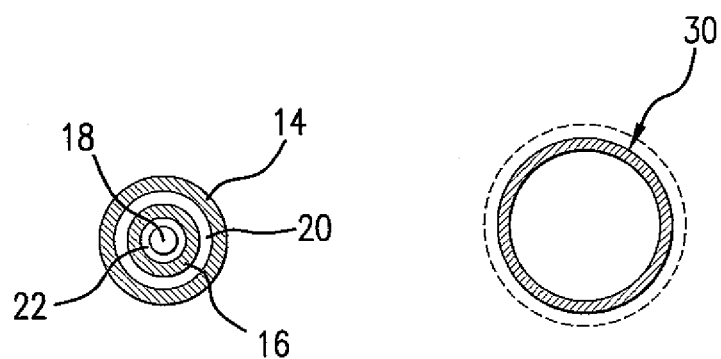
FIG. 1　　FIG. 1A　　FIG. 1B

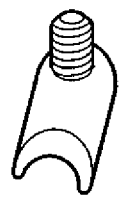 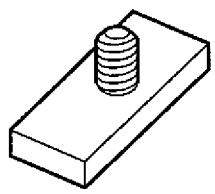 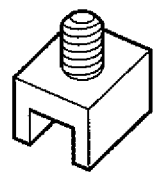 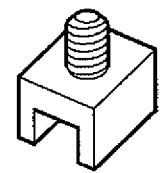
FIG. 7A  FIG. 7B  FIG. 7C  FIG. 7D
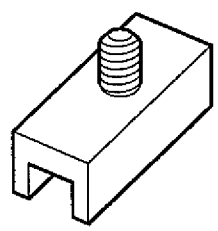 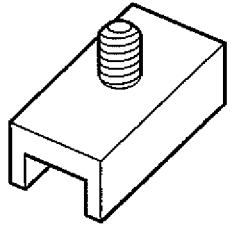 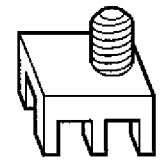 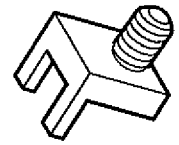
FIG. 7E  FIG. 7F  FIG. 7G  FIG. 7H

MAINTAINING A FIXED DISTANCE DURING COATING OF DRUG COATED BALLOON

CROSS-REFERENCE TO RELATED APPLICATION

This application claims priority to U.S. Provisional Application No. 61/345,569 entitled "Maintaining a fixed distance during coating of drug coated balloon," filed May 17, 2010 which is incorporated herein by reference in its entirety.

BACKGROUND OF THE DISCLOSED SUBJECT MATTER

1. Field of the Disclosed Subject Matter

The presently disclosed subject matter is related to the delivery of therapeutic agents from an interventional medical device. More particularly, the presently disclosed subject matter relates to an interventional device for delivery of therapeutic agents from an expandable member, such as a balloon. The disclosed subject matter also relates to a method and apparatus for maintaining a fixed distance between a dispenser and the balloon surface during application of one or more therapeutic agents onto the expandable member as well as the assembly of the medical device.

2. Description of Related Subject Matter

Atherosclerosis is a syndrome affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. Dissection, or perforation, of the blood vessel is another complication of angioplasty that can be improved by stenting. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis). Examples of various known drug eluting stents are disclosed in U.S. Pat. Nos. 5,649,977; 5,464,650; 5,591,227, 7,378,105; 7,445,792; 7,335,227, each of which are hereby incorporated by reference in their entirety. However, a drawback of drug eluting stents is a condition known as late stent thrombosis. This is an event where a blood clot forms inside the stent, which can occlude blood flow.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7 percent restenosis and 4.8% MACE (major adverse coronary events) as compared to patients treated with drug eluting stents, in which restenosis was 20.8 percent and 22.0 percent MACE rate. (See, PEPCAD II study, Rotenburg, Germany)

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time may be longer for a peripheral procedure, however typically even for peripheral procedures the balloon is expanded for less than 5 minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent.

Furthermore, conventional techniques for applying a coating, such as a therapeutic agent, may not be desirable for coating balloons, or other expandable members of medical devices. Such convention techniques include spraying (air-atomization, ultrasonic, electrostatic, etc.), dip-coating, spin-coating, vapor deposition, roll coating, micro-droplet coating, etc. Balloons present a cylindrical surface to be coated where it is desired to uniformly coat only the working length of the balloon and no other portion of the balloon or catheter. Techniques such as spraying are needed to coat the fine geometry of stents without webbing but are very inefficient, with a low coating efficiency. However, balloons do not have this requirement and the low drug utilization efficiency is undesirable, particularly for large peripheral balloons. Many of these conventional techniques do not provide sufficient coating uniformity or edge control. For example, it is often desirable to apply the coating to balloon surface when the balloon is at least partially inflated, however balloons which are not cylindrical in shape when expanded, such as peripheral balloons, often warp or bow upon inflation. Consequently, a non-uniform coating is applied to the balloon surface thereby leading to a non-uniform drug distribution with even the potential for bare spot with no coating. In addition, this compromises the efficiency in the coating process, can degrade the efficacy of the therapeutic agent, and an inappropriate coating process can lead to further distorting or bowing of the balloon.

Thus there remains a need, and an aim of the disclosed subject matter is directed towards, maintaining a fixed distance between the coating dispenser and the surface of the balloon during the application of one or more therapeutic agents to the surface of an expandable member of a medical device.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system and method of coating an expandable member of a medical device. The system and corresponding method comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween. From the fixed distance, fluid is applied from the at least one outlet to form a controlled coating of fluid on the surface of the expandable member along the coating path.

The substantially fixed distance between the expandable member and the at least one outlet is maintained by displacing the expandable member relative to the at least one outlet. For example, maintaining the substantially fixed distance can include constraining displacement of the expandable member during relative movement between the at least one outlet and the surface of the expandable member. Constraining displacement can include providing a guide to constrain displacement of the expandable member in at least one direction during relative movement between the at least one outlet and the surface of the expandable member.

In some embodiments, the guide includes at least one constraining member having at least one discrete point of a contact with the surface of the expandable member. Alternatively, the guide can include at least two constraining members contacting generally opposing sides of the expandable member. Alternatively, the guide is a generally U-shaped member having three discrete points of contact with the surface of the expandable member. Alternatively, the guide substantially surrounds a perimeter of the expandable member.

The amount of displacement can vary along a length of the expandable member. For example, the amount of displacement can increase along a length of the expandable member. The expandable member can at least be partially expanded prior to dispensing fluid to the surface of the expandable member.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

FIG. 1 is a schematic side view representative balloon catheter in accordance with the disclosed subject matter.

FIG. 1A is a cross-sectional view taken along lines A-A in FIG. 1.

FIG. 1B is a cross-sectional view taken along lines B-B in FIG. 1.

FIGS. 7A-H are schematic views of alternative embodiments of a guide to displace an expandable member in accordance with the disclosed subject matter.

DETAILED DESCRIPTION

Figure 2:
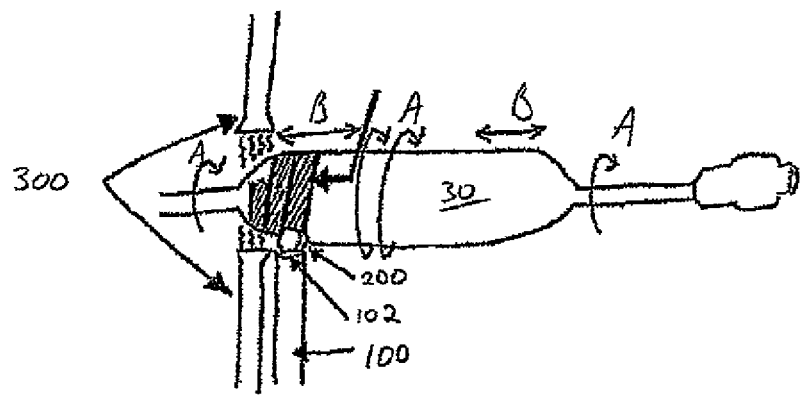
FIG. 2 is a schematic representation of a direct fluid coating process and system.

Reference will now be made in detail to the embodiments of the disclosed subject matter, an example of which is illustrated in the accompanying drawings. The method and corresponding steps of the disclosed subject matter will be described in conjunction with the detailed description of the system.

The methods and systems presented herein can be used for applying one or more coatings to a medical device. The disclosed subject matter is particularly suited for applying a uniform coating of therapeutic agents, and other fluid compounds, to select portions of an expandable member. While the disclosed subject matter references application of a fluid to an expandable member, it is to be understood that the methods and systems disclosed herein can also be employed to apply therapeutic, polymeric, or matrix coatings to various surfaces of medical devices, as so desired.

The disclosed subject matter provides a method, and corresponding system, to coat an expandable member, or select portions thereof, by a variety of application processes while maintaining a substantially fixed distance between the outlet of the applicator and the surface of the expandable member. In one embodiment, the expandable member can be coated by a direct fluid coating application process; however alternative coating methods can be employed in accordance with the disclosed subject matter. The direct fluid coating applies a coating without atomization, or the formation of droplets, of the coating fluid. Additionally, the direct fluid coating process improves the efficiency of the dispensing of a coating solution, which can be controlled based on the volume of coating solution dispensed, rather than via a weight based control. Indeed, the direct fluid coating process provides a system and method for dispensing of a coating solution which can achieve 95.0% or greater transfer efficiency, i.e., 95.0% of the coating solution dispensed is applied to the expandable member.

In accordance with the disclosed subject matter, a system and corresponding method of coating an expandable member of a medical device comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween. From the fixed distance, fluid is applied from the at least one outlet to form a coating of fluid on the surface of the expandable member along the coating path. For embodiments utilizing the direct fluid coating process, fluid is dispensed from the dispenser to form a substantially continuous bead of fluid between the outlet and the surface of the expandable member along the coating path.

For purpose of explanation and illustration, and not limitation, an embodiment of a medical device having an expandable member is shown schematically in FIGS. 1 and 1A. Particularly, and as illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein, has an outer surface and an inner surface disposed at the distal end portion of the catheter shaft. In accordance with the disclosed subject matter, a coating is applied to at least a portion of the outer surface of the balloon.

The elongated catheter shaft 12 comprises an outer tubular member 14 and an inner tubular member 16. The outer tubular member 14 defines an inflation lumen 20 disposed between the proximal end portion and the distal end portion of the catheter shaft 12. Specifically, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the inflation medium, i.e. provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 defines the guidewire lumen 22 for the guidewire 18. Although FIGS. 1 and 1b illustrate the guidewire lumen as having an over-the-wire (OTW) construction, the guidewire lumen can be configured as a rapid-exchange (RX) construction, as is well known in the art.

A wide variety of balloon catheters and balloon constructs are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane, polyesters, polyester copolymers, and polyethylene. Examples of other balloon and catheter embodiments which can be employed in accordance with the disclosed subject matter include U.S. Pat. Nos. 4,748,982; 5,496,346; 5,626,600; 5,300,085, 6,406,457 and application Ser. Nos. 12/371,426; 11/539,944; 12/371,422, each of which is hereby incorporated by reference in their entirety.

In one embodiment, the coating is applied to the expandable member of the fully assembled medical device. As described above with reference to FIGS. 1, 1A-B, medical devices such as the catheter 10 include a plurality of components which are typically manufactured as separate discrete components and thereafter assembled together. Applying a coating to the expandable member at an upstream stage of an assembly line requires extensive measures to minimize or prevent the coating from being exposed to various equipment and processes during the downstream portion of the assembly line. Such exposure can render the coating prone to damage and/or contamination during final assembly of the catheter, and can result in scrapping of the entire catheter. In order to avoid such exposure and damage to the coating in conventional catheter assembly lines additional equipment including monitoring and safety controls would be required. Accordingly, applying the coating to the expandable member of a fully assembled catheter avoids the unnecessary complexity, and excessive costs associated with such a modified assembly line.

In accordance with the disclosed subject matter, any of a variety of fluid compositions can be applied to the expandable member. For example, the fluid can include a therapeutic agent for treatment of a disease state. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector. However, the therapeutic agents include, cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotaroliumus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel.

Additionally, or alternatively, the fluid can include other compounds or additives, such as polymers, binding agents, plasticizers, solvents, surfactants, additives, chelators, fillers, and the like. Examples of possible compounds include zotarolimus, polyvinylpyrrolidone and glycerol. In one embodiment the therapeutic agent can be provided in liquid form or dissolved in a suitable solvent. In another embodiment, the therapeutic agent is provided as a particulate and mixed in a suitable carrier for application as a fluid.

In accordance with an aspect of the disclosed subject matter, a variety of techniques for applying a coating of therapeutic agent can be employed, such as direct fluid coating, spraying (air-atomization, ultrasonic, electrostatic, etc.), jetting, vapor deposition, micro-droplet coating, etc. For example, the dispenser apparatus and corresponding coating techniques disclosed in U.S. Pat. No. 7,455,876 and U.S. Patent Application Publication No. 2010/0055294, the entirety of each is hereby incorporated by reference, can be employed in accordance with the disclosed subject matter.

An embodiment of the coating process and system of the disclosed subject matter is illustrated in FIG. 2 for purpose of explanation and not limitation. The dispenser depicted herein is shown as a pipet or tube 100 having an outlet positioned proximate expandable member 30 such that the fluid dispensed from the pipet is in continuous fluid contact with the expandable member 30 without atomization of the coating solution. As the coating solution is delivered from a fluid source, e.g. reservoir (not shown), through the dispenser outlet, a continuous fluid medium or bead 200 of solution directly contacts the surface of the expandable member. FIG. 2 depicts the pipet 100 generally at a right angle to the balloon surface. However, alternative alignments and orientations can be used as desired or needed for the type and dimensions of expandable members.

A positive pressure is applied to assist with dispensing fluid from the outlet. In addition, due to capillary action, the surface tension pulls the bead of coating solution 200 onto the surface of the expandable member. Furthermore, the outlet can be heated prior to and/or during the dispensing of the coating solution. The heating of the dispenser can reduce the viscosity of the coating solution and therefore accelerate the coating process as well as reduce the potential for clogging or occluding of the dispenser outlet 102. FIG. 2 depicts the outlet generally at a right angle to the balloon surface.

Coating process and systems of the disclosed subject matter can be performed with the expandable member in a fully or partially inflated condition, or even in a deflated condition. When deflated, the expandable member can be pleated, folded, wrinkled or pressed. In the embodiment illustrated in FIG. 2, the expandable member is fully inflated to allow coating of all or select portions of the outer surface. Additionally, the temperature of expansion medium, or the expandable member itself, can be controlled to further manipulate the contour of the expandable member.

As the fluid is delivered from the dispenser, relative movement is established between the dispenser 100 and the expandable member 30 to effect a continuous, or patterned coating path as desired. For example, and as depicted in FIG. 2, the coating path can define a continuous spiral or helical pattern along the outer surface of the expandable member. Alternatively, coating paths can be established such as discrete circumferential rings, discrete lines extending along the expandable members longitudinal axis, and combinations thereof. Hence, the relative movement can include rotation, translation, or combinations thereof, of either, or both, the expandable member 30 and the dispenser 100.

For example, the expandable member 30 can be rotated about its central axis, as shown by arrows A in FIG. 2, and simultaneously translated along the central axis, as shown by arrow B in FIG. 2. Additionally, or alternatively the expandable member 30 can rotate relative a first axis, and the dispenser 100 translate relative a second axis, e.g., to define a helical coating path. Accordingly, any number of coating paths can be selected and provided on the expandable member. The various movements described herein can be performed simultaneously, sequentially, continuously or intermittently, as so desired.

Movement of the medical device and/or the outlet of the dispenser is accomplished by providing a support assembly. The support assembly can maintain the position of one element, e.g. the dispenser, while allowing movement of the other element, e.g., the medical device. Alternatively, the support assembly can allow movement of both elements. Movement can be performed manually, or by providing a drive assembly with suitable drive source, such as a motor or the like, and appropriate controller as know in the art.

Simultaneous with the relative movement, the fluid is dispensed from the outlet to form a continuous bead between the outlet and the surface of the expandable member along the coating path. Generally, it has been determined that the formation and maintenance of the continuous bead of fluid will be a function of the fluid density, and average velocity of the fluid from the outlet. In one embodiment, the Reynolds number, i.e. ratio of momentum or inertial force to viscosity, for the flow out of the outlet is less than 2300 such that the flow remains substantially laminar. The Reynolds number being defined by the equation $Re=(\rho*v*l)/\mu$, wherein "l" is a dimension of the outlet.

The desired portions of the expandable member can be coated with a single pass or cycle of relative movement between the expandable member and dispenser. Alternatively, a plurality of passes or cycles of coating operation discussed above can be performed. Such multiple passes or cycles allows for further variation in the coating properties along the expandable member length. For example, one portion of the expandable member can be coated with a different number of coating layers of fluid than another portion of the expandable member thereby creating a gradient of the coating solution on the expandable member. Further, the methods and apparatus of the disclosed subject matter can be employed to apply layers of different coating compositions to the expandable member. For example, therapeutic-free primers, concentrated therapeutic layers, and drug-excipient layers can be applied. As discussed above, varied coating properties allow for greater flexibility and customization of the catheter to provide a greater range of applications and ability to meet patient needs.

In accordance with another aspect of the disclosed subject matter, a drying apparatus can be employed to accelerate the coating process. As shown in FIG. 2, a dryer 300 can be positioned downstream of the dispenser to apply heat, forced gas, cooled gas, vacuum, infra-red energy, microwave energy, or a combination thereof to the surface of the expandable member. The drying nozzle may also be collinear or coaxial with the dispenser by either circumscribing it or by have the dispenser surround it as with an annular opening. In some embodiments, a drying operation can be conducted between successive coating passes or cycles. Additionally, or alternatively, the drying operation can be conducted concurrently with a coating pass or cycle, as depicted in FIG. 2. Similar to the dispenser 100 discussed above, the drying apparatus 300 can be oriented at any angle between 0°-90° with respect to the expandable member, and be configured for relative movement.

While the dispenser of the embodiment illustrated in FIG. 2 depicts a dispenser configured as a pipet, additional or alternative dispensers can be employed. Some examples of such dispensers include flexible tubing, coaxial tubing, hypotubes, dies, ball-bearing dispense tubing, syringe, needles, brushes, sponges, cones and foam applicators. Furthermore, FIG. 2 depicts a dispenser having a single outlet 102 perpendicular to the expandable member though alternative angles between 0°-90° can be employed. Also, the use of a plurality of outlets can be employed. Each outlet can be oriented perpendicular, disposed adjacent each other along the axis of the expandable member, and/or spaced circumferentially about the expandable member.

In this regard, a plurality of reservoirs containing distinct coating solutions can be provided with each dispenser in fluid communication with a separate reservoir. As with the outlet of FIG. 2, the dispensers can be positioned at various locations and orientations relative to the expandable member. Additionally, the expandable member 30 can be oriented in a generally horizontal position, as shown in FIG. 2, vertically, or at or at any angle between 0°-90°, if desired. Orienting the expandable member in a vertical configuration can be advantageous in larger size expandable members, e.g. peripheral balloons, since the gravitational force acts parallel the expandable member's longitudinal axis thereby preventing deformation such as arching or bowing of the expandable member and associated catheter shaft, which the expandable member can be susceptible to when in the horizontal position.

As previously noted, and in accordance with the disclosed subject matter, the dispenser is maintained at a predetermined or fixed distance from the expandable member surface. Maintaining a fixed distance between the dispenser outlet and the expandable member, in combination with rotation and translation as discussed above, provides greater control over the coating pattern to be applied to the expandable member surface. Such control can be advantageous by providing a consistent and uniform dosage of the therapeutic agent along the surface of the expandable member, resulting in a balanced expandable member.

Additionally, maintaining a fixed distance between the dispenser outlet and the expandable member surface reduces the amount of waste or excess coating which is not retained on the expandable member. For example, with spray coating techniques, the amount of waste or excess coating generally increases with the distance between the outlet(s) and the surface of the expandable member. For example, with direct coating techniques, discrete droplets of fluid could form if the distance between the outlet and the surface of the expandable member were too great. Conversely, if the distance between the dispenser outlet and the expandable member surface were too small, undesired or accidental contact between the dispenser outlet and expandable member surface can occur resulting in tearing or scratching of the expandable member surface or abrasion to the coating applied to the expandable member. The distance between the outlet and the surface of the expandable member can depend upon a number of variables, including viscosity of the fluid, surface tension of the fluid, pump rate of the fluid, diameter of the dispenser exit orifice, volatility of the solvents in the fluid, speed at which the fluid is dispensed and/or size of the outlet opening. For example, when using a pipet type dispenser, the distance between the outlet and the surface generally should be less than 40 times the smallest cross dimension of the outlet.

The fixed distance between the outlet and the surface of the expandable member can be monitored and maintained in a number of ways in accordance with the disclosed subject matter. For example, the fixed distance can be maintained between the dispenser outlet and the expandable member surface by constraining displacement of the expandable member via a guide member during relative movement. Constraining displacement provided by the guide ensures that the surface of the expandable member exiting the guide is accurately positioned in a predetermined location. In other words, as a bowed or otherwise non-cylindrical expandable member enters the guide, the surface contour of the expandable member is forced to comply with the geometry of the guide, resulting in a predictable and constant location of the expandable member upon exiting the guide. Accordingly, the expandable member can be maintained in an intentionally bowed or deformed shape during a coating cycle.

Based on this known or predetermined location of the expandable member exiting the guide, the applicator (e.g. spray nozzle, pipet, etc.) is disposed a predetermined distance from the guide member such that a controlled and uniform coating is applied over the desired length of the expandable member. Further, the predetermined distance between the dispensing means and the guide can be adjusted as so desired to accommodate various sizes of expandable members, as well as various sizes or types of dispensers.

The guide can be positioned proximate the dispenser outlet to avoid contact with the newly dispensed coating from the outlet. For example, the guide can be positioned laterally adjacent to the dispenser outlet, or distal the dispenser outlet provided the guide does not lie in a path in which it might encounter a fresh or wet coating. The guide can be coated with or fabricated of a durable, low friction material such as thermoplastic and thermoset polymers. Examples of which include, for purpose of illustration and not limitation, polyethylene, polypropylene, polytetraflouroethylene (PTFE), fluorinated ethylene propylene (FEP), poly(vinylidene fluoride) (PVDF), poly(tetraflouroethylene-co-ethylene), and nylons.

Figure 3A:
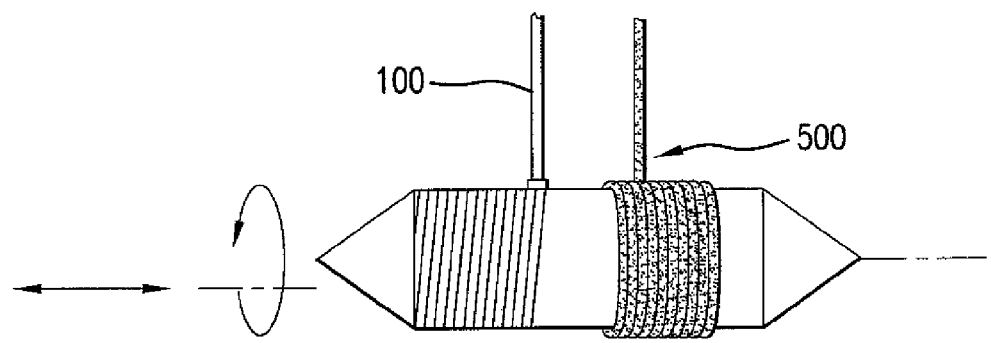
FIGS. 3A-D are schematic views of various embodiments of a guide to contrain an expandable member in accordance with the disclosed subject matter.
Figure 3B:
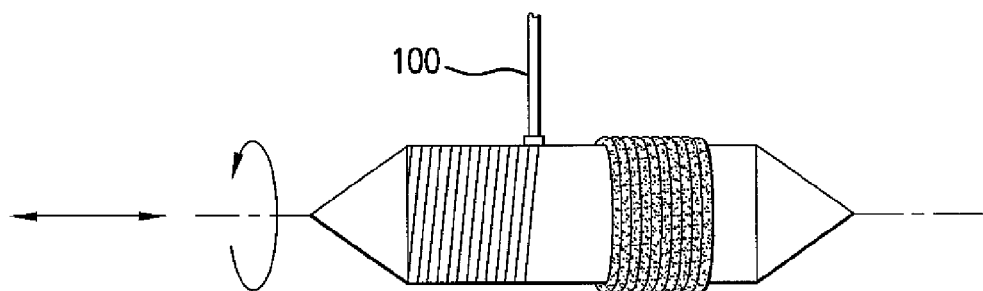

In the embodiments illustrated in FIGS. 3A-D, a guide 500 serves as a constraining member and is configured as a collar which circumscribes and/or houses the expandable member. The guide 500 is formed having a length and material of sufficient rigidity to maintain the expandable member in a fixed geometry. The guide 500 is capable of moving, e.g. translating along the expandable member's longitudinal axis. For example, the guide 500 can be mounted above the expandable member, as shown in FIG. 3A, or below the expandable member as shown in FIG. 3B for such movement. The guide 500 is rigidly attached to a mounting member 600 which is configured to translate along rail 602. Rail 602 is arranged in a parallel manner to the longitudinal axis of the expandable member such that the guide 500 can translate relative to the expandable member during the coating process. Alternatively, the guide 500 can be a single-piece member with a fixed size in which the expandable member is inserted inside or through the guide prior to application of the coating. Additionally, or alternatively, the guide 500, and dispenser 100, can be fixed in place and the expandable member translated-rotated relative to them.

Figure 3C:
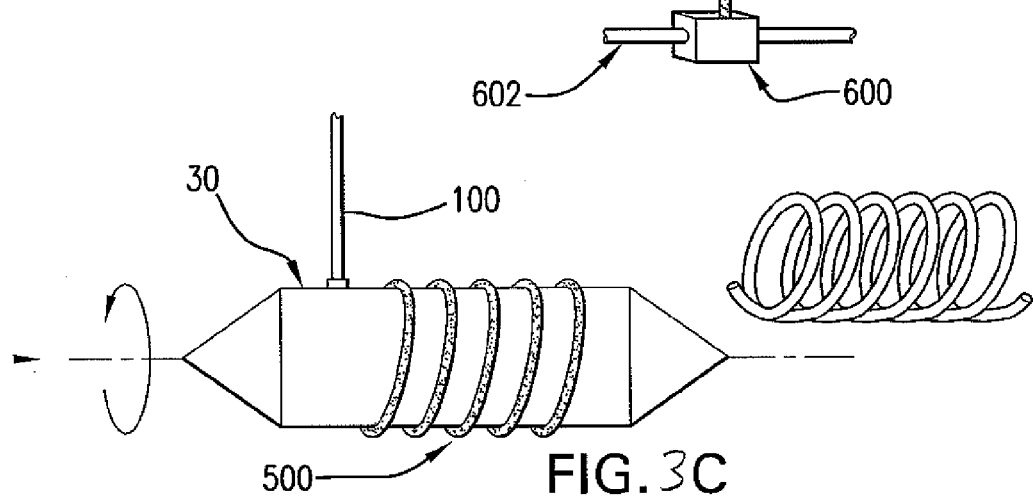
Figure 3D:
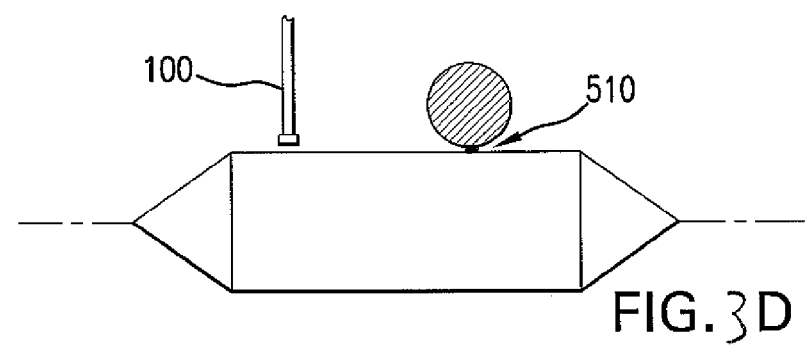

The embodiments of FIGS. 3A-B depict a guide 500 in the form of a continuous collar which circumscribes a portion of the expandable member. FIG. 3C depicts an embodiment of the guide 500 in the form of a spring-like structure. Such a spring-like or helical support structure is advantageous in that it provides sufficient rigidity and support to the expandable member, while reducing the surface area of the expandable member in contact with the guide, thereby reducing friction and the risk of damage to the coating layer or expandable member surface. As shown in FIG. 3D, which depicts a cross-sectional view of a single spiral element of the guide of FIG. 3C, the amount of surface area of the expandable member in contact with the guide is localized to a discrete point of contact 510.

Figure 4:
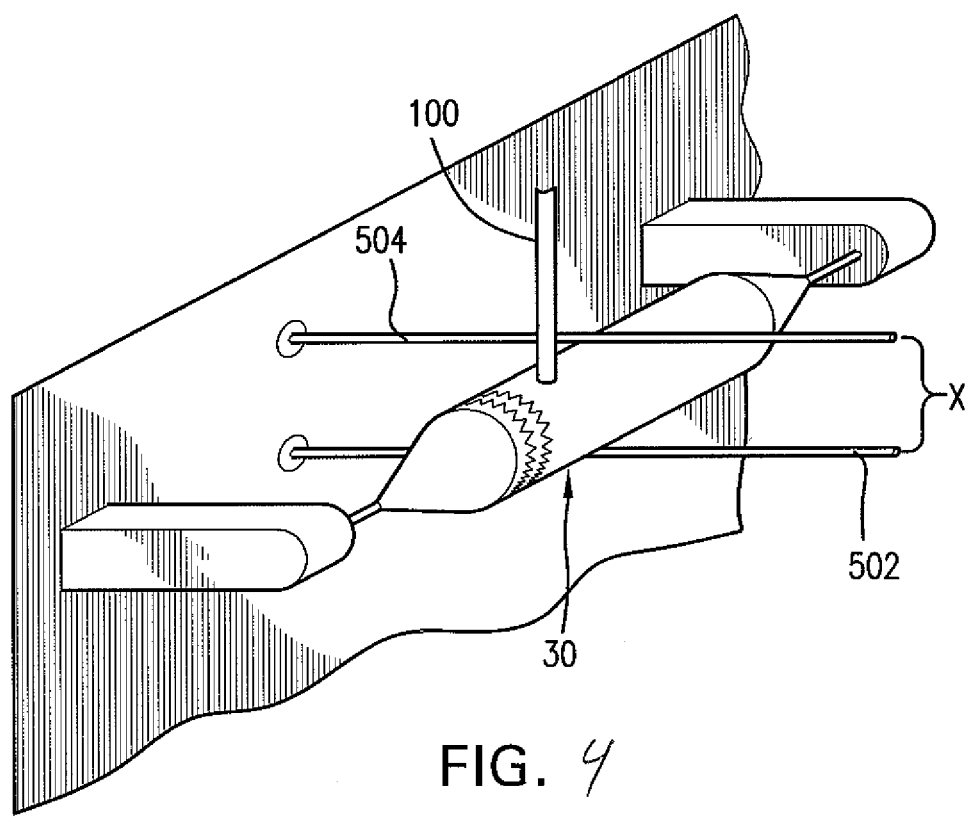
FIGS. 4-6 are schematic views of alternative embodiments of a guide for displacing an expandable member in accordance with the disclosed subject matter.
Figure 5:
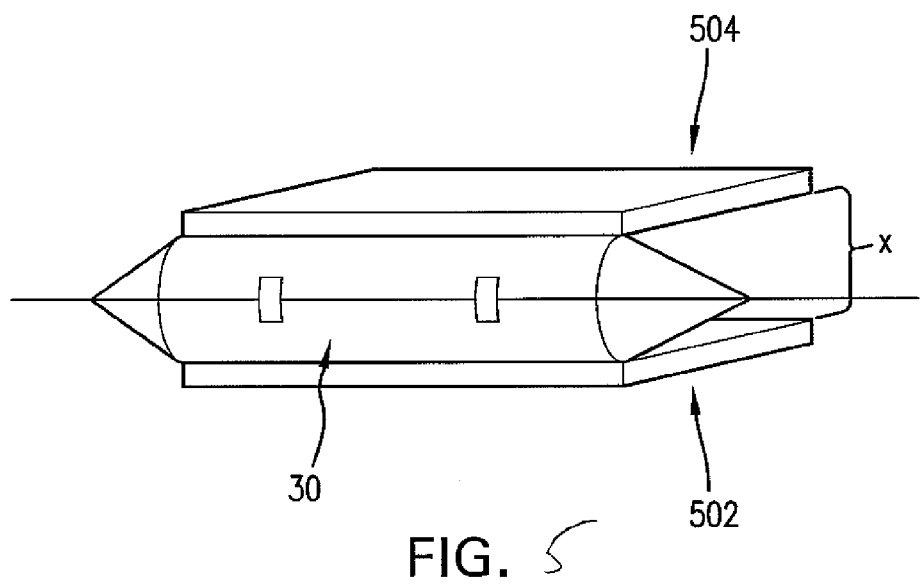

In an alternative embodiment, the guide depicted in FIG. 4 includes a plurality of pins 502, 504 disposed on opposite sides the expandable member. The pins 502, 504 can be oriented at any angle less than 90 degrees depending on the dimensions of the expandable member and can be mounted to a fixture as stationary members, or moved relative to the expandable member. Additionally, the pins 502, 504 are provided with a fixed spacing therebetween thus ensuring accurate positioning of the expandable member exiting the pins 502, 504 irrespective of any bowing or otherwise asymmetrical shape of the expandable member. Similar to the embodiment of FIG. 3C, the discrete surface contact established by the pins 502, 504 provides sufficient rigidity and support to the expandable member, while reducing the surface area of the expandable member in contact with the guide, thereby reducing friction and the risk of damage to the coating layer or expandable member surface. As an alternative to the pins 502, 504 as illustrated in FIG. 5, elongated plates can be utilized in a similar fashion such that the plates are diametrically opposed on opposite sides of the expandable member and constrain any displacement of the expandable member proximate the plates. Each plate can be configured to engage the expandable member tangentially at a discrete line of contact. In either embodiment, the pins or plates provide discrete points of contact. Furthermore, the pins or plates can be repositioned to accommodate expandable members of varying sizes. If so desired, a lubricant can be applied to the guide to inhibit or prevent the generation of frictional forces during operation.

Figure 6:
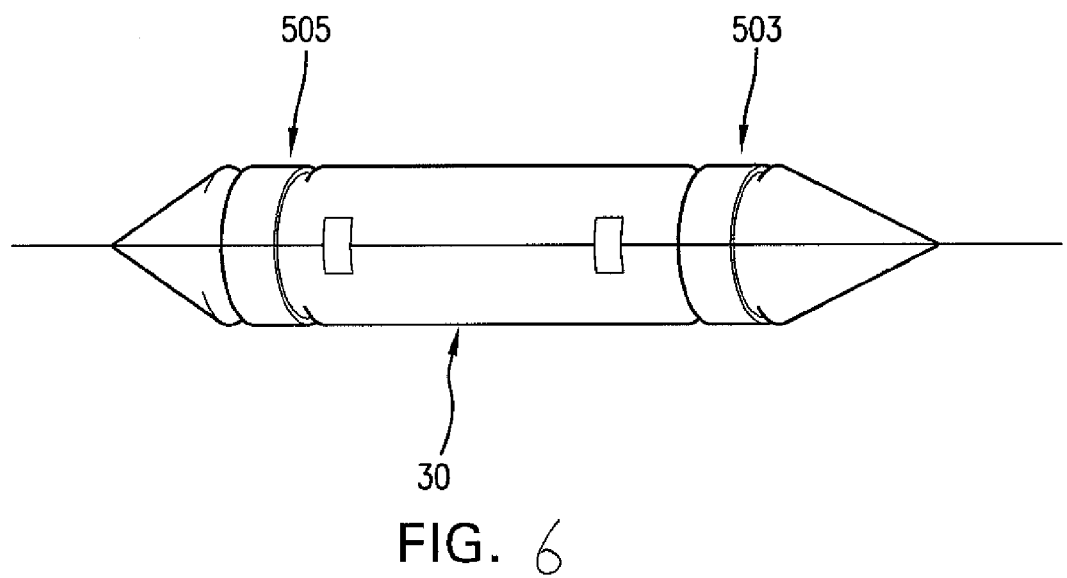

Alternatively, or additionally, stabilizing shoulder cones, as illustrated in FIG. 6, can be positioned in contact with the shoulders of the expandable member, defined as the transition region between the working length and tapered sections of the expandable member. Further, the guide can be configured with an inner diameter which is smaller than the outer diameter of the expandable member. Upon insertion of the expandable member 30 within the guide 500, the expandable member would be slightly deformed to counteract any bowing tendencies of the expandable member. Further, the guide 500 can be configured as tubing or chambers, which are inflatable/ deflatable such that dynamic pressurization of the collars 500 could occur to offset any bowing effect. For example a proximal collar 503 could be inflated to a different pressure than distal collar 505.

In accordance with another aspect of the disclosed subject matter, the guide can be provided in the form of a channel which captures or receives a portion of the expandable member. With reference to FIGS. 7A-7H, for purpose of illustration and not limitation, the channel can be provided with a variety of shapes and dimensions. For example, FIG. 7A depicts a guide or channel having a partial cylindrical shape with an inner diameter generally corresponding to the diameter of the inflated expandable member. FIGS. 7B-F depict various guides of different lengths, each with a generally rectangular cross-section to define three locations of contact with the expandable member. FIGS. 7G-H each depict a guide having a top plate to contact the expandable member along a discrete line, and depending legs to engage the expandable member at discrete points of contact.

In the embodiment of FIG. 7H, the guide can be configured as a yoke to depresses individual or multiple sections of the surface of the expandable member while the fluid is dispensed onto the surface of the expandable member. In this manner, as the relative movement is established between the dispenser outlet and the expandable member, the area of the expandable member proximate the guide remains at a fixed and predictable position during the coating cycle.

According to another aspect of the disclosed subject matter, the guide can include a plurality of constraining members of various dimensions and sizes that can be arranged in series. For example, a series of progressively narrower guides can be arranged to receive and constrain or deform the expandable member. Furthermore, it is to be understood that the dimensions and size of the guides can be varied to accommodate a variety of expandable members. The guides of the disclosed subject matter can be formed from any suitable material, non-limiting examples of which include PTFE, poly (etheretherketone) (PEEK), FEP, PVDF, aluminum and stainless steel.

Figure 8:
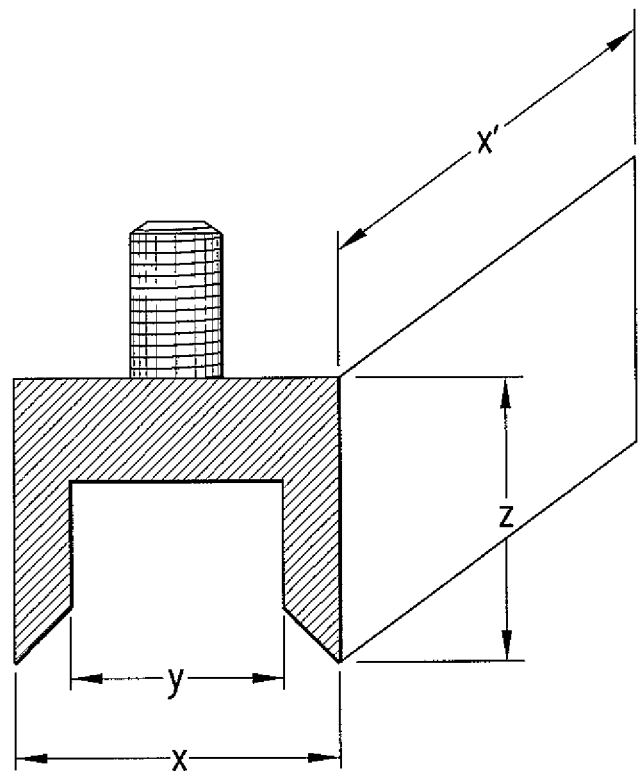
FIG. 8 is a schematic cross-sectional view of the guide embodiment shown in FIG. 7H.

The guide 500 can be formed in a variety of dimensions selected to suit the particular application and dimensions of the expandable member. As discussed above, a series of guides of varying dimensions can be aligned to progressively constrain the expandable member. For example, and with reference to the guide of FIG. 8, guides for use with expandable members of 5.0 mm and 6.0 mm can be configured with the dimensions provided in Table 1 below.

| Dimension | Guide 1 | Guide 2 | Guide 3 | Guide 4 |
| --- | --- | --- | --- | --- |
| x (mm) | 5.15 +/− 0.05 | 6.15 +/− 0.05 | 5.15 +/− 0.05 | 6.15 +/− 0.05 |
| y (mm) | 4.9 +/− 0.05 | 5.9 +/− 0.05 | 4.9 +/− 0.05 | 5.9 +/− 0.05 |
| z (mm) | 7.5 +/− 0.1 | 7.5 +/− 0.1 | 7.5 +/− 0.1 | 7.5 +/− 0.1 |
| length ($x^1$) (mm) | 10 | 10 | 20 | 20 |

Figure 9:
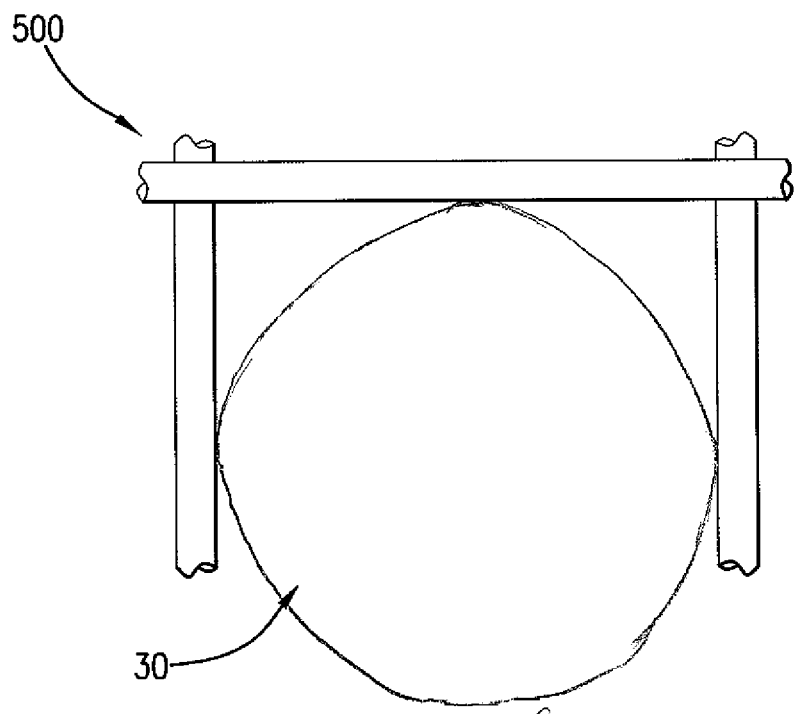
FIG. 9 is a schematic front view of a guide in accordance with an aspect of the disclosed subject matter.

Alternatively, and as shown in FIG. 9, the guide can be constructed from pins or rods rather than plates or collars, to minimize the contact between the guide 500 and the expandable member 30. Similarly, the depending legs of the guide in FIGS. 7G-H, likewise can be formed as rods or pins. This configuration provides three discrete points of contact between the expandable member and guide, thereby minimizing the risk of damage to the coating layer or expandable member surface. This minimal contact between the expandable member and the guide is advantageous in reducing the forces required to establish the relative movement between the expandable member and the dispenser outlet. For purpose of illustration, an expandable member exhibiting a 2 mm bow, which is defined as the amount of deflection from the longitudinal axis of the expandable member, was constrained within the guide of FIG. 7H to reduce the bow to 0.5 mm.

Figure 10:
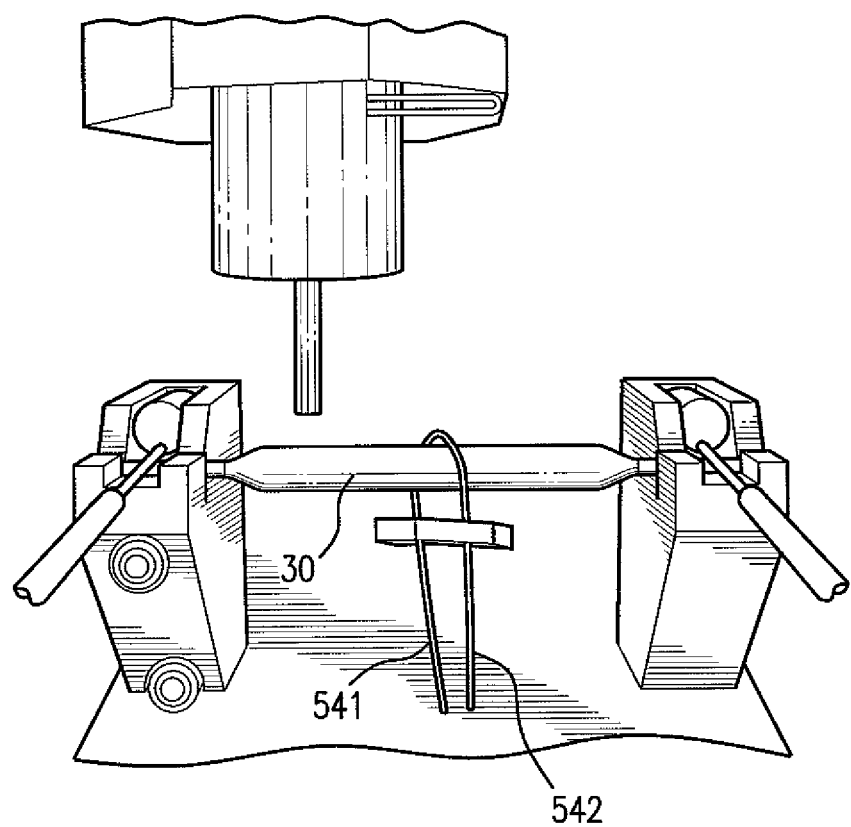
FIG. 10 is a schematic view of alternative embodiment of a guide in accordance with an aspect of the disclosed subject matter.
Figure 11:
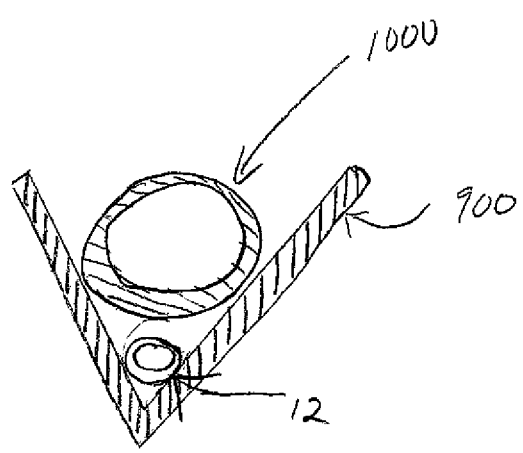
FIG. 11 is a schematic cross-sectional view of a support assembly for supporting the shaft of the catheter during a coating process.

In an alternative embodiment, the guide can be configured as a weighted anchor having two wire-like members 541, 542 draped over and in contact with the expandable member 30, as shown in FIG. 10. The wire-like members can be made of teflon, delrin, PPE, or any other material having a suitable coefficient of friction to avoid damaging the expandable member, or coating disposed thereon. The weight of the anchor portion, as well as the dimensions and cross-sectional shape of the wire-like members 541, 542 can vary depending on the properties of the expandable member, and the desired amount of deformation desired.

As discussed above, the coating method and system of the disclosed subject matter can be performed on a previously assembled medical device, e.g. balloon catheters. Often the force required to rotate or otherwise move the expandable member is applied to a location, and/or component, proximal of the expandable member. Therefore, significant force may be required to overcome the friction and inertia of the various components of the medical device in order to achieve movement of the expandable member. Thus, any reduction or minimization of points of contact between the guide and expandable member is advantageous as the frictional forces generated during the relative movement will in turn be minimized, thereby reducing the amount of force required by the support assembly, or manual operator, to establish relative movement. As the proximal components of medical device are often polymeric and not torsionally rigid, undue friction on the expandable member can lead to torsional loading and unloading of the proximal members. This leads to inconsistent rotation of the medical device, which in turns leads to non-uniform coating. Additionally, the presence of undue frictional forces is undesired in that if the expandable member were to be accidentally released from the guide, any coating applied could be undesirably smeared or discharged from the expandable member due to the reactionary force of the expandable member.

If desired, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths can be porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson, the disclosure of which is incorporated by reference in its entirety.

In accordance with in the disclosed subject matter, an endoprosthesis, e.g. stent, can be mounted on the expandable member. The type of stent that can be used includes, but is not limited to, bare metal stent, drug eluting stent, bioabsorbable stent, balloon-expandable stent, self-expanding stent, prohealing stent, and self-expanding vulnerable plaque implant. The expandable member can be coated independently of the stent or in conjunction with the stent coating process. The stent coating can contain the same or different therapeutic agents from the catheter or expandable member. However, the particular coating on the catheter or expandable member has distinct release kinetics from the therapeutic coating on the stent. The coating applied to the expandable member can be allowed to dry prior to placement of the stent thereon.

Alternatively, the coating could not be allowed to dry or cure past a "tacky" state before the stent is positioned and/or crimped onto it. This would enable the adhesion of the coating on the expandable member to the inside of the prosthesis. This process increases the retention of the prosthesis onto the expandable member (acting as a prosthesis retention enhancer) thus reducing the chance that the stent will move on the expandable member during the torturous delivery through the vascular lumen While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method of coating an expandable member of a medical device, comprising:
providing an expandable member having an inflated configuration, wherein the expandable member is transversly displaceable along its length in the inflated configuration;
providing an applicator in fluid communication with a fluid source, the applicator having at least one outlet for applying fluid therefrom;
positioning the applicator proximate a surface of the expandable member in the inflated configuration;
establishing relative movement between the at least one outlet and the surface of the expandable member along a coating path;
maintaining a substantially fixed distance between the at least one outlet and the surface of the expandable member during relative movement therebetween by externally constraining transverse displacement of the expandable member proximate the at least one outlet during relative movement therebetween; and
applying fluid from the at least one outlet to form a direct coating of fluid on the surface of the expandable member along the coating path.

2. The method of claim 1, wherein externally constraining displacement includes providing a guide laterally adjacent to the at least one outlet to constrain transverse displacement of the expandable member in at least one direction during relative movement between the at least one outlet and the surface of the expandable member.

3. The method of claim 2, wherein the guide includes at least one constraining member having at least one discrete location of contact with the surface of the expandable member.

4. The method of claim 2, wherein the guide includes at least two constraining members contacting generally opposing sides of the expandable member.

5. The method of claim 2, wherein the guide is a generally U-shaped member having three discrete locations of contact with the surface of the expandable member.

6. The method of claim 2, wherein the guide substantially surrounds a perimeter of the expandable member.

7. The method of claim 1, wherein an amount of constrainment of the expandable member varies along a length of the expandable member.

8. The method of claim 7, wherein the amount of constrainment of the expandable member increases along a length of the expandable member.

9. The method of claim 1, wherein the inflated configuration of the expandable member is partially inflated while dispensing fluid to the surface of the expandable member.

10. The method of claim 1, wherein the guide is made of polyethylene, polypropylene, poly(tetrafluoroethylene), fluorinated ethylene propylene (FEP), poly(vinylidene fluoride), poly(tetrafluoroethylene-co-ethylene), PEEK, or nylon.

11. The method of claim 1, wherein applying fluid is dispensed to form a substantially continuous bead of fluid between the outlet and the surface of the expandable member along the coating path.

* * * * *